(12) United States Patent
Park

(10) Patent No.: US 12,376,991 B2
(45) Date of Patent: Aug. 5, 2025

(54) SCLERAL BUCKLE FOR ALLEVIATION OF RETINAL DETACHMENT AND REFRACTIVE ERROR

(71) Applicant: Robert I. Park, Asheville, NC (US)

(72) Inventor: Robert I. Park, Asheville, NC (US)

( * ) Notice: Subject to any disclaimer, the term of this patent is extended or adjusted under 35 U.S.C. 154(b) by 880 days.

(21) Appl. No.: 17/625,250

(22) PCT Filed: Jul. 8, 2020

(86) PCT No.: PCT/US2020/041285
§ 371 (c)(1),
(2) Date: Jan. 6, 2022

(87) PCT Pub. No.: WO2021/007374
PCT Pub. Date: Jan. 14, 2021

(65) Prior Publication Data
US 2022/0241109 A1  Aug. 4, 2022

Related U.S. Application Data

(60) Provisional application No. 62/871,481, filed on Jul. 8, 2019.

(51) Int. Cl.
*A61F 9/007* (2006.01)
*A61F 2/14* (2006.01)
*A61F 9/00* (2006.01)

(52) U.S. Cl.
CPC .......... *A61F 9/00727* (2013.01); *A61F 2/147* (2013.01); *A61F 9/0017* (2013.01)

(58) Field of Classification Search
CPC .... A61F 9/00727; A61F 9/0017; A61F 2/147; A61F 2250/0007; A61F 2002/0081
See application file for complete search history.

(56) References Cited

U.S. PATENT DOCUMENTS

| | | |
|---|---|---|
| 6,511,508 B1 | 1/2003 | Shahinpoor et al. |
| 9,962,255 B1 | 5/2018 | Weiss |
| 2004/0098126 A1 | 5/2004 | Freeman et al. |
| 2014/0074128 A1 | 3/2014 | Park |
| 2019/0117382 A1 | 4/2019 | Kahook |

FOREIGN PATENT DOCUMENTS

WO   2021007374 A1   1/2021

*Primary Examiner* — Javier G Blanco
(74) *Attorney, Agent, or Firm* — NGUYEN TARBET IP LAW

(57) ABSTRACT

A rhegmatogenous retinal detachment (RRD) occurs when a tear in the retina leads to fluid accumulation with a separation of the neurosensory retina from the underlying retinal pigment epithelial (RPE); this is the most common type of retinal detachment and can lead to blindness. The present invention features an eye shape modification (ESM) system (a scleral buckle) for the prevention and repair of retinal detachment as well for the adjustment of refractive error and the prevention of induced refractive error caused by scleral buckles. The present invention creates a scleral buckle with protuberances on the interior surface of the buckle. These protuberances produce corrugation/indentations in the eye which allows for both axial and circumferential relaxation. Additionally, the present invention creates on scleral buckle that remove excess bulky material from the scleral buckle band, producing a scleral buckle that is easier and safer to surgically implant onto the eye.

7 Claims, 9 Drawing Sheets

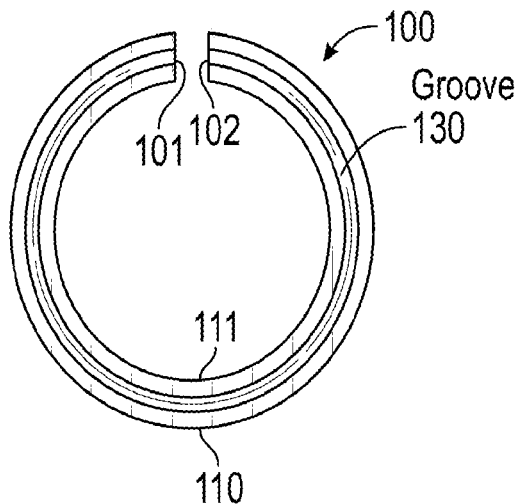
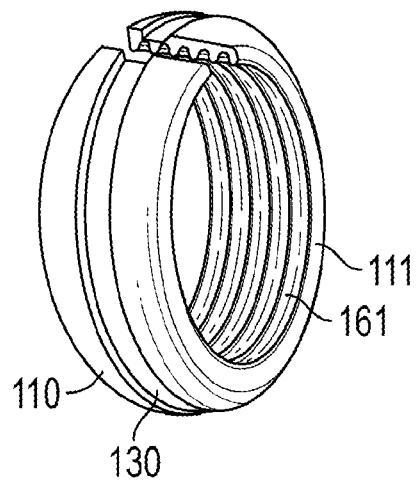
FIG. 2A
FIG. 2B
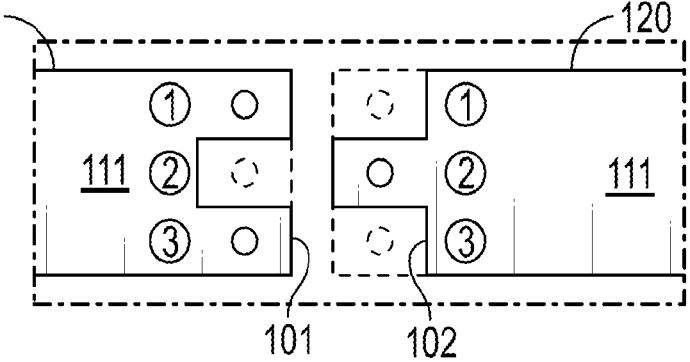
FIG. 3A
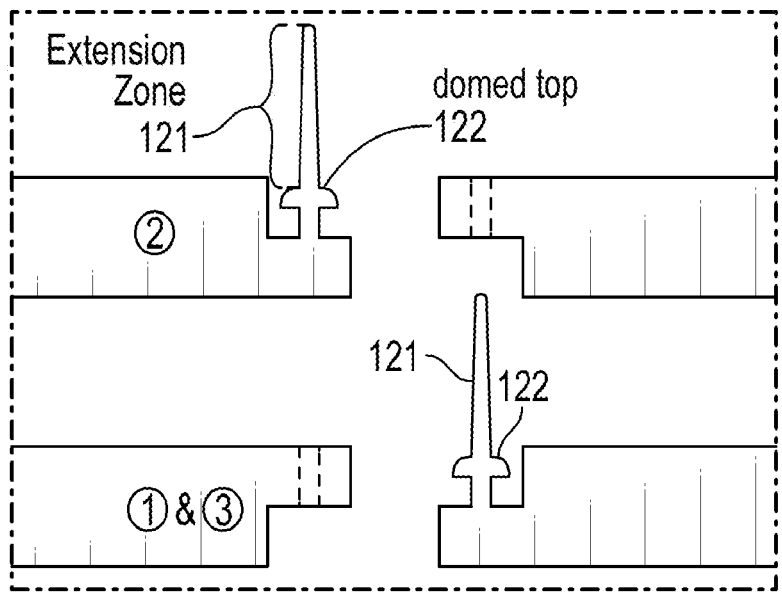
FIG. 3B

SCLERAL BUCKLE FOR ALLEVIATION OF RETINAL DETACHMENT AND REFRACTIVE ERROR

CROSS-REFERENCES TO RELATED APPLICATIONS

This application claims benefit of U.S. Patent Application No. 62/871,481 filed Jul. 8, 2019, the specification(s) of which is incorporated herein in its entirety.

FIELD OF THE INVENTION

The present invention relates to methods and devices for modifying eye shape, more particularly, scleral buckles and related technologies used for the prevention and repair of retinal detachment, especially rhegmatogenous retinal detachment (RRD). The present invention further relates to methods and devices that can alter or change the shape of the eye, namely, to allow for the adjustment of refractive error and the prevention of induced refractive error caused by a scleral buckle.

BACKGROUND OF THE INVENTION

Rhegmatogenous retinal detachment (RRD) is a potentially blinding disease that affects 1 in 10,000 people. RRD generally develops in eyes in a two-step fashion. First, excess traction on the retina from the vitreous gel inside the eye causes a retinal tear. This initiating event is a result of an increase in vitreoretinal traction, typically from vitreous breakdown. Second, persistent traction on a retinal tear, typically a so-called "horseshoe tear," causes retinal elevation, allowing vitreous fluid to track underneath the retina and enter the sub-retinal space, causing a separation of the photoreceptor layer from the underlying retinal pigment epithelium. Shearing of the retina from the underlying retinal pigment epithelium results in RRD. Generally, if RRD is left untreated, blindness occurs.

The process by which retinal detachment occurs is well documented clinically and experimentally. A series of classic experiments on RRD clearly demonstrated the importance of vitreoretinal traction in the development of RRD. Recently, data regarding the overall shapes and dimensions of eyes in emmetropia and myopia has been determined in vivo by surface coil MRI scanning. This new information can be used to understand which eyes are at the greatest risk for retinal detachment and how to repair them.

Furthermore, MRI data regarding myopic eyes can help to understand the impact of myopic eye dimensions on intraretinal stress. Myopic globes are an order of magnitude, longer, higher, and wider than emmetropic eyes. Myopic globes have thinner retinas horizontally but not vertically than emmetropic globes. The result of the dimensional differences is that circumferential intraretinal stress increases with increased myopia in the vertical and horizontal dimensions and the axial stress increases with increased axial length. The larger eyes of myopes also results in increased acceleration and deceleration of the retina during eye movement with concomitant increased tractional forces. Consequently, myopes have eyes with increased retinal stress at static baseline and with eye movement and an increased risk of developing RRD. Conversely, hyperopic eyes are shorter, narrower, and lower than emmetropes. Thus, hyperopes have small eyes and have a decreased risk of RRD.

Without wishing to limit the present invention to any theory or mechanism, the current model of RRD implicates vitreoretinal traction as the primary cause of retinal detachment. According to the model, vitreoretinal traction induces a retinal tear and persistent traction causes separation of the photoreceptors from the underlying retinal pigment epithelial (RPE) cells. Vitreous fluid overwhelms the RPE pump and RRD ensues.

Biomechanically, the insults causing RRD may be divided into two events: the retinal tear and the actual separation of the retina from the RPE. The retinal tear is no different than failure of any other structure. Failure or fracture of a structure occurs when the stress (defined as the force per cross sectional area) in the structure is high enough to overcome the inherent strength of a material.

As discussed, the primary component in generation of retinal detachments is increased vitreoretinal traction. Although the resultant vitreoretinal traction is difficult to quantify, the following generalizations can be made regarding the effect of globe dimensions on vitreoretinal traction: (1) axial traction is the greatest, which may be a contributing cause of early posterior vitreous detachment; (2) vertical traction is next most significant; and (3) horizontal traction is also increased, contributing to increased intraretinal stress, tearing, and retinal detachments. The increased vitreoretinal traction when combined with increased intrinsic intraretinal stress and gravity makes retinal tears and RRD more likely in myopes.

Increased intraretinal stress can also lead to tearing of the retina. The stress can be from vitreoretinal traction but can also come from other sources. Intrinsic intraretinal stress depends on the retinal thickness and eye shape and is guided by LaPlace's law. LaPlace's law essentially states that at a constant intraocular pressure, as the radius of the eye increases, the wall tension or force in the wall increases. Thus, increasing the radius of the eye increases the intraretinal stress. Thinner retinas also have increased intraretinal stress because the inherent wall tension must be carried by a smaller cross-sectional area.

RRD treatments include pars plana vitrectomy, pneumatic retinopexy, or scleral buckling. In pars plana vitrectomy, the vitreous gel is dissected and removed from the eye to relieve the vitreoretinal traction. Fluid may be drained from under the retina. The retinal tear is treated with laser photocoagulation or cryoretinopexy to induce scarring and seal the hole in the retina. A gas tamponade may be used to close the retinal hole and stabilize the retina while the hole heals. In pneumatic retinopexy, a gas bubble is placed in the eye to block fluid from entering the retinal hole. The retinal tear is treated with laser photocoagulation or cryoretinopexy to induce permanent closure of the tear.

In scleral buckling to repair retinal detachment, an encircling band and/or scleral buckle element may be placed around the eye or be stitched to the surface of the eye to decrease vitreoretinal traction, close a retinal hole, and reduce intraretinal stress. Generally, in scleral buckling, the conjunctiva and the Tenon's capsule are dissected from the sclera and a scleral buckling element, usually a piece of inert plastic or silicone rubber, solid or sponge, is used to indent the eye. The scleral buckle element may be sutured into place directly or may be held in place with an encircling band (imagine a belt wrapped around a balloon). The indentation closes the hole created by the retinal tear and allows reabsorption of fluids from under the retina and resolution of the RRD. The edges of the retinal tear are treated with laser photocoagulation or cryoretinopexy to permanently seal the tear and prevent further fluid migration under the retina. A gas bubble may or may not be used to further seal the tear from an interior approach and subretinal fluid may or may not be removed through the sclera.

Scleral buckles have several biomechanical effects on the eye. Specifically, a moderate height-encircling band reduces the ocular circumference and diameter, normalizes the shape of the globe (making it rounder), and reverses the force vector of preretinal membranes. The net effect is a reduction in both the intraretinal stress and vitreoretinal traction (drivers of RRD). Caution must be taken though in the degree of indentation because excessively high buckles increase intraretinal stress and can elevate the retina at the buckle edges. The result of excessive indentation is an increased risk in tears and re-detachment. Conversely, too shallow of indentation results in an ineffective scleral buckling effect.

The present invention can be used to repair retinal detachments like a traditional scleral buckle but can also be used to reduce not just the circumferential intraretinal stress in patients at high risk of retinal detachment but also the axial intraretinal stress, making retinal detachment less likely. The reduction in intraretinal stress occurs through reduction of axial length and equatorial diameter in a controlled fashion. In the hyperopic eye with a retinal detachment, the globe can be elongated with the present invention scleral buckle while the ocular circumference is reduced; this allows diminishment of vitreoretinal traction and circumferential stress while correcting refractive error. The refractive effect of shortening or lengthening of the axial length is to reduce the amount of refractive error and to allow focusing of light further posteriorly in the eye, thereby alleviating myopia and/or hyperopia.

Without wishing to limit the present invention to any theory or mechanism, it is believed that the methods and systems of the present invention are advantageous because they provide the design of a calibrated system for eye shape modification (ESM), utilize an ESM device to repair retinal detachments and reduce the risk of recurrent detachment, limit further horizontal or vertical expansion of the eye in myopia, lengthen the eye in hyperopia, and depending on the embodiment in question, reduce the axial length in myopic eyes, thereby alleviating myopia.

BRIEF SUMMARY OF THE INVENTION

It is an objective of the present invention to provides an eye shape modification device (scleral buckle) that allows for the formation of corrugations/indentations in the eye (like an accordion) and helps to prevent and repair of retinal detachment, adjust for refractive error and prevent induced refractive error by a scleral buckle, as specified in the independent claims. Embodiments of the invention are given in the dependent claims. Embodiments of the present invention can be freely combined with each other if they are not mutually exclusive.

The present invention may help to remodel the eye globe to reduce biomechanical risk of retinal detachment, change refractive error, prevent myopia progression, and/or alleviate myopia and hyperopia. The methods and system of the present invention may be safer and easier to surgically implant as compared to traditional scleral buckles. Additionally, without wishing to limit the present invention to any theory or mechanism, it is believed that the present invention features the first scleral buckle that is not only effective in preventing myopia progression but is also effective in alleviating existing myopia.

In some aspects, the present invention may feature a scleral buckle comprising a scleral buckle first end and an opposite scleral buckle second end, a scleral buckle exterior surface and an opposite scleral buckle interior surface (FIG. 1A and FIG. 2A). In some embodiments, the scleral buckle interior surface contains a plurality of protuberances disposed thereon. In other embodiments the scleral buckle first end and scleral buckle second end are shorter than the scleral buckle third end and scleral buckle fourth end. In further embodiments, the scleral buckle is adapted to be wrapped around the eye by the scleral buckle first end and the scleral buckle second end being brought and held together such that the plurality of protuberances on the interior surface makes contact with a surface of the eye.

In some embodiments, the present invention may feature a scleral buckle (FIGS. 5A and 6A) comprising a scleral buckle first end and an opposite scleral buckle second end, a scleral buckle third end and an opposite scleral buckle fourth end, a scleral buckle exterior surface and an opposite scleral buckle interior surface. The scleral buckle may comprise plurality of linkage sections running perpendicular between the scleral buckle third end and the scleral buckle forth end. In some embodiments, the scleral buckle comprises a series of indentation ridges running parallel between the scleral buckle third end and the scleral buckle forth end wherein each indentation ridge is in between the linkage sections. In some embodiments, the scleral buckle comprises a plurality of open sections between the indentation ridges and the linkage sections. In further embodiments, the scleral buckle is adapted to be wrapped around the eye by the scleral buckle first end and the scleral buckle second end being brought and held together.

In further embodiments, the present invention may feature a method of scleral buckling the eye. In some embodiments, the method comprises of inserting the scleral buckle underneath the rectus muscles of the eye, connecting the scleral buckle first end and the scleral buckle second end, and suturing the scleral buckle to the sclera with sutures.

One of the unique and inventive technical features of the present invention is the design of the scleral buckle that creates corrugations/indentations in the eye (like an accordion) that allows for either lengthening or shortening of the eye. Without wishing to limit the invention to any theory or mechanism, it is believed that the technical feature of the present invention advantageously provides for the simultaneous relaxation of the retina both circumferentially and axially. Additionally, the design of the present invention allows for the scleral buckle to be safely and easily implanted. None of the presently known prior references or work has the unique inventive technical feature of the present invention.

Moreover, the prior references teach away from the present invention. For example, previous designs for a scleral buckle only allows for the retina to be relaxed circumferentially, however, this can result in the flattening of the normal curvature of the eye, causing axial elongation. Additionally, previous designs that allow for the reduction of axial length through aggressive indentations have an unwanted side effect of increasing intraretinal stress and therefore cause an increased risk for further retinal tears. Furthermore, aggressive buckling increases intraretinal stress in the areas adjacent to the buckle, making additional retinal tears and tensional retinal detachments more likely.

Without wishing to limit the present invention to any theory or mechanism, the present invention can therefore be used to repair retinal detachment, reduce risk of retinal detachment, and to normalize or shorten the axial length of the eye, thus reducing the myopia induced by scleral buckling or alleviating existing myopia.

Without wishing to limit the present invention to any theory or mechanism, the device of the present invention can be used in patients with myopia but no retinal detachment to alleviate myopia and simultaneously reduce the risk of retinal detachment. Without wishing to limit the present invention to any theory or mechanism, a version of the device may also be used to induce emmetropia and correct hyperopia.

Without wishing to limit the present invention to any theory of mechanism, the device of the present invention can be used in emmetropic patients with increased equatorial diameter, to alleviate the risk of retinal detachment or to treat retinal detachment without changing refractive error.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The present invention is not limited to the configurations shown in the figures. The features and advantages of the present invention will become apparent from a consideration of the following detailed description presented in connection with the accompanying drawings in which:

FIG. 1A is a front perspective view of a non-limiting embodiment of a scleral buckle of the present invention.

FIG. 1B shows the scleral buckle (of FIG. 1A) flattened out, the scleral buckle comprises of a first end opposite a second end, and a third end opposite a fourth end along with an exterior surface opposite an interior surface. A connector region is disposed perpendicularly on the first end and the second end. The connector region has an extension zone and a domed top. The scleral buckle interior surface comprising circumferential ridges.

FIGS. 2A-2B show a scleral buckle with a groove indentation disposed along the exterior surface of the buckle. A circular silicone band is placed into the groove of the scleral buckle to bring the first end and the second end together with a silicone tube.

FIG. 3A shows a zoomed-in top view of the scleral buckle connector regions. The connector regions comprise of three segments that interlock together.

FIG. 3B shows a zoomed-in side view of the scleral buckle connector regions. The extension zone is threaded through a hole on the opposite side of the scleral buckle (e.g. the extension zone on the first end is threaded through a hole on the second end of the scleral buckle). The extension zone is threaded through the hole until the domed top is passed through the hole. Once secured, the extension zone may be shortened.

Figure 4A:
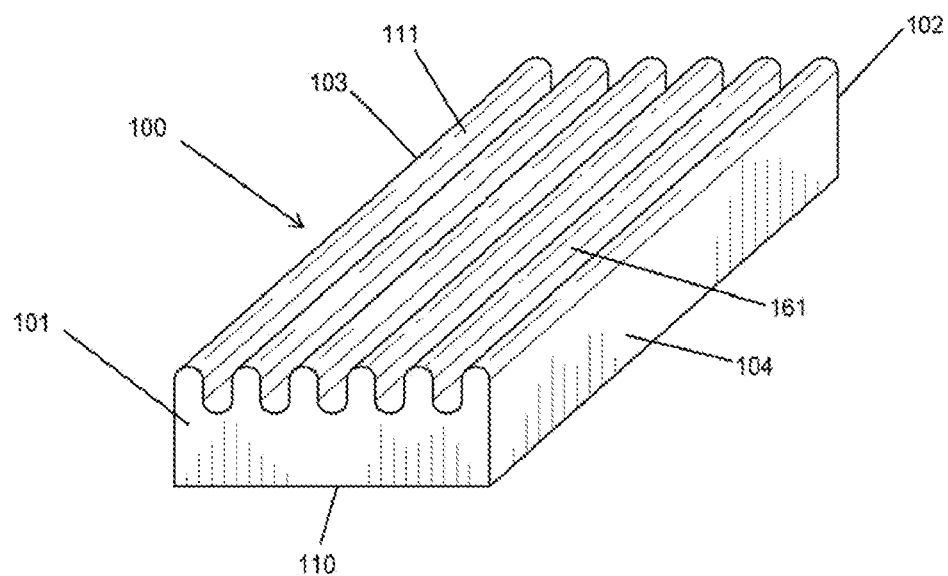
Figure 4B:
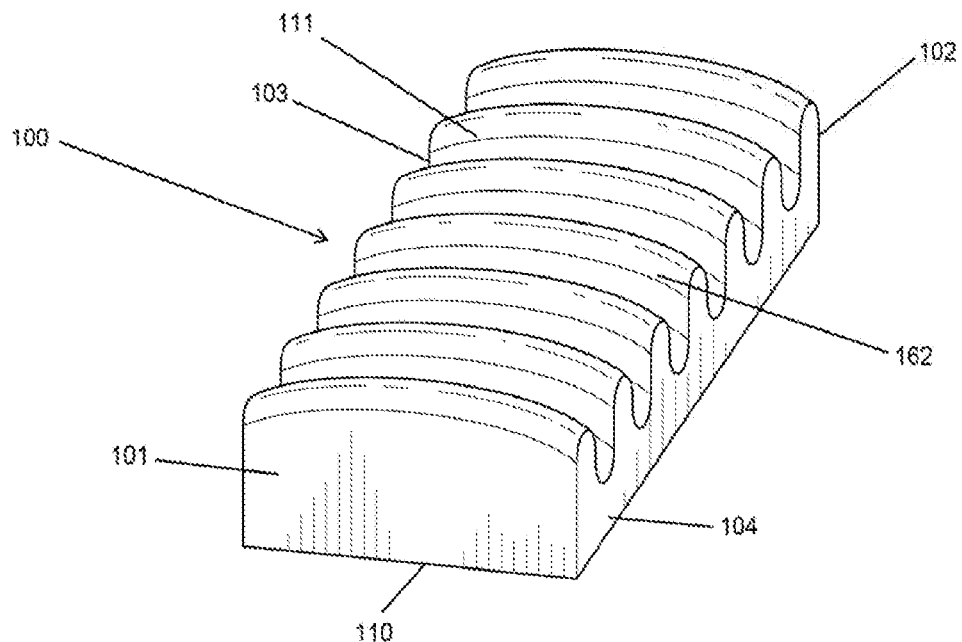
Figure 4C:
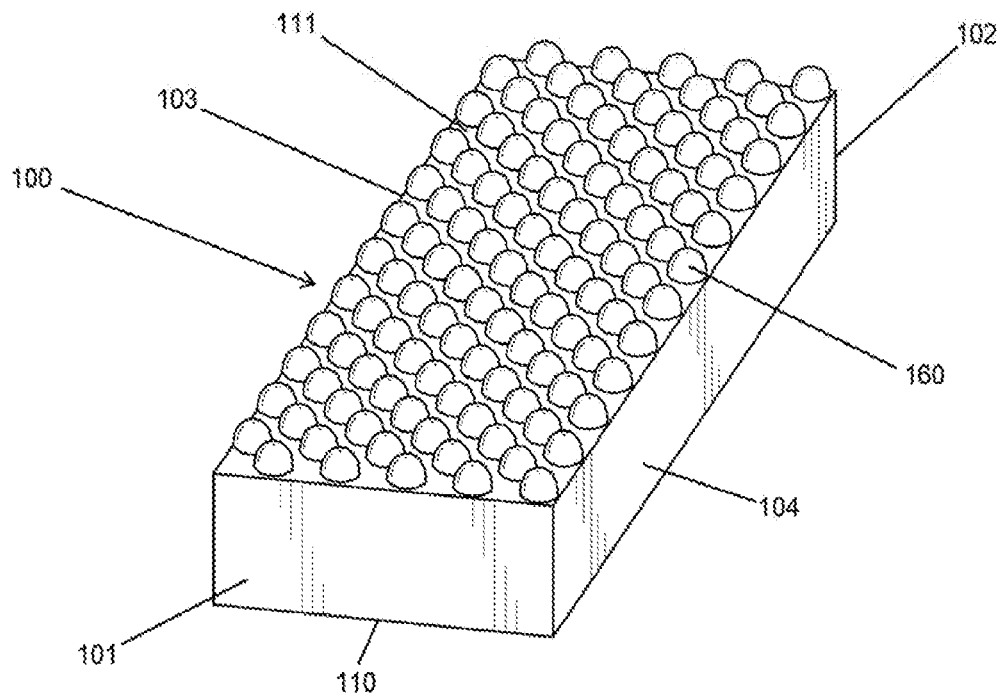
Figure 4D:
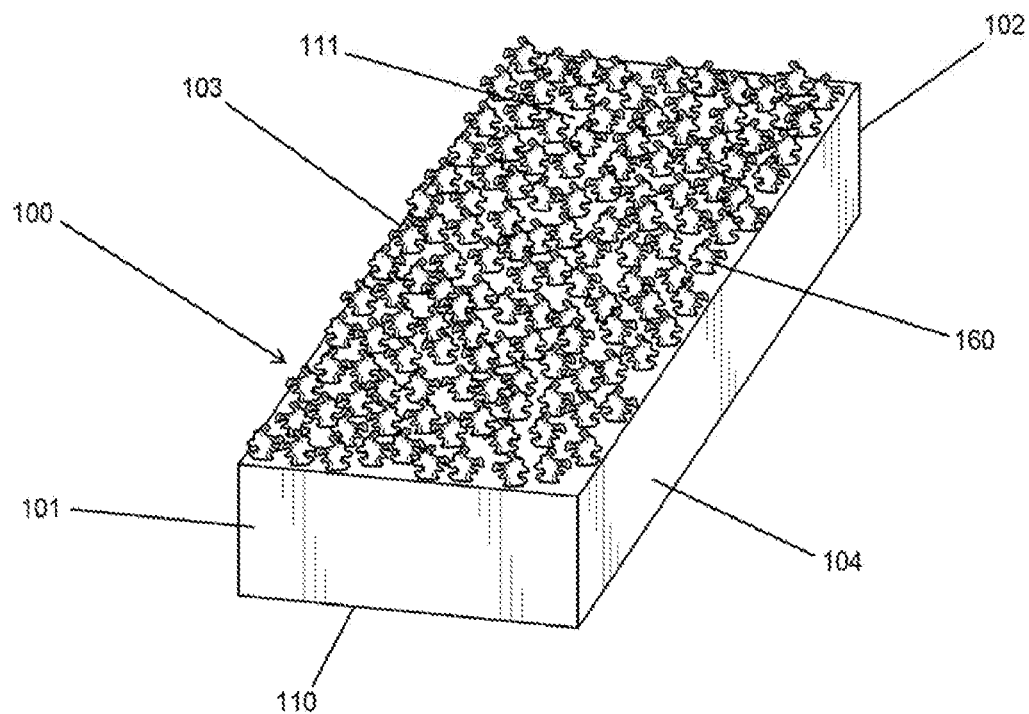

FIGS. 4A-4D show isometric views of embodiments of the scleral buckle having circumferential ridges (FIG. 4A), axial ridges (FIG. 4B), uniform raised protuberances (FIG. 4C) and irregular raised protuberances (FIG. 4D). The scleral buckle exterior surface can be flat (as depicted), convex, or concave.

Figure 5A:
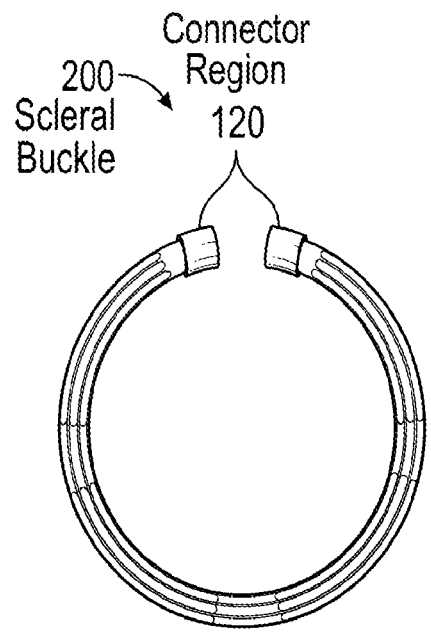

FIG. 5A shows a front perspective view of another embodiment of the scleral buckle.

Figure 5B:
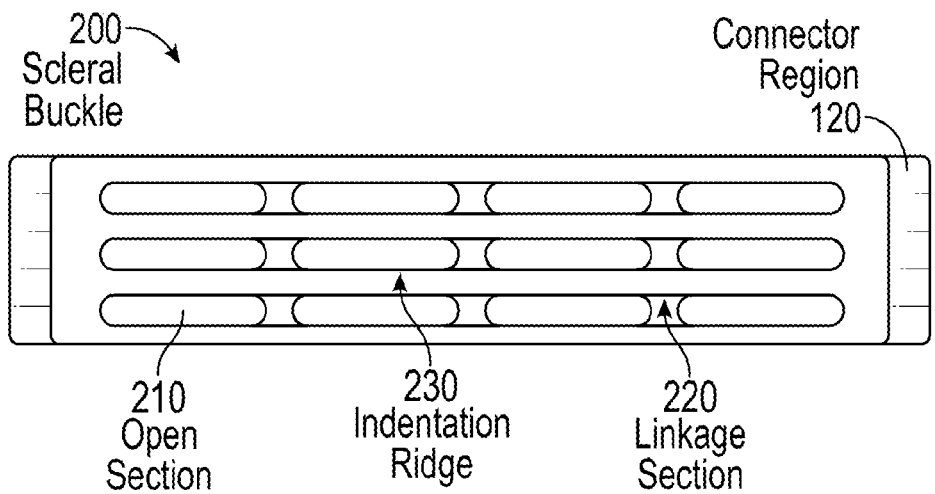

FIG. 5B shows a top view of the scleral buckle flattened out.

Figure 5C:
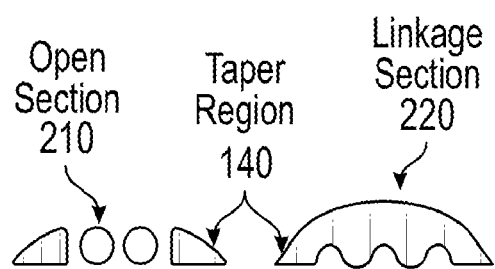

FIG. 5C shows cross-sectional views of an open section and a linkage section of the scleral buckle, both the open section and the linkage section have a tapered region along the third end and fourth end.

Figure 5D:
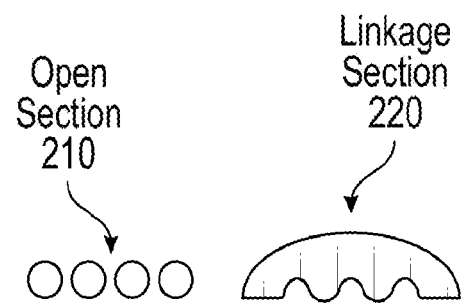

FIG. 5D shows cross-sectional views of the open section and the linkage section having rounded edges along the third end and fourth end.

Figure 6A:
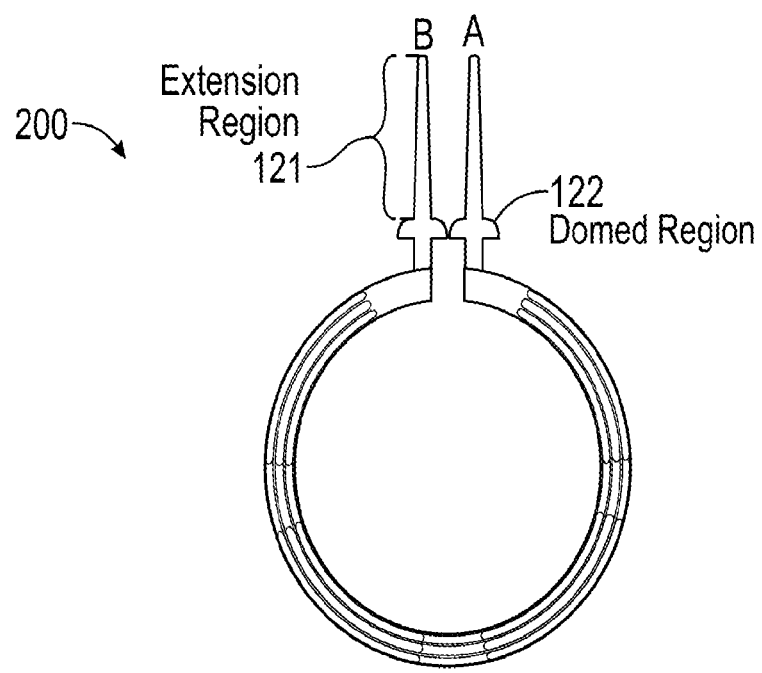

FIG. 6A shows another embodiment of the scleral buckle with a connector region.

Figure 6B:
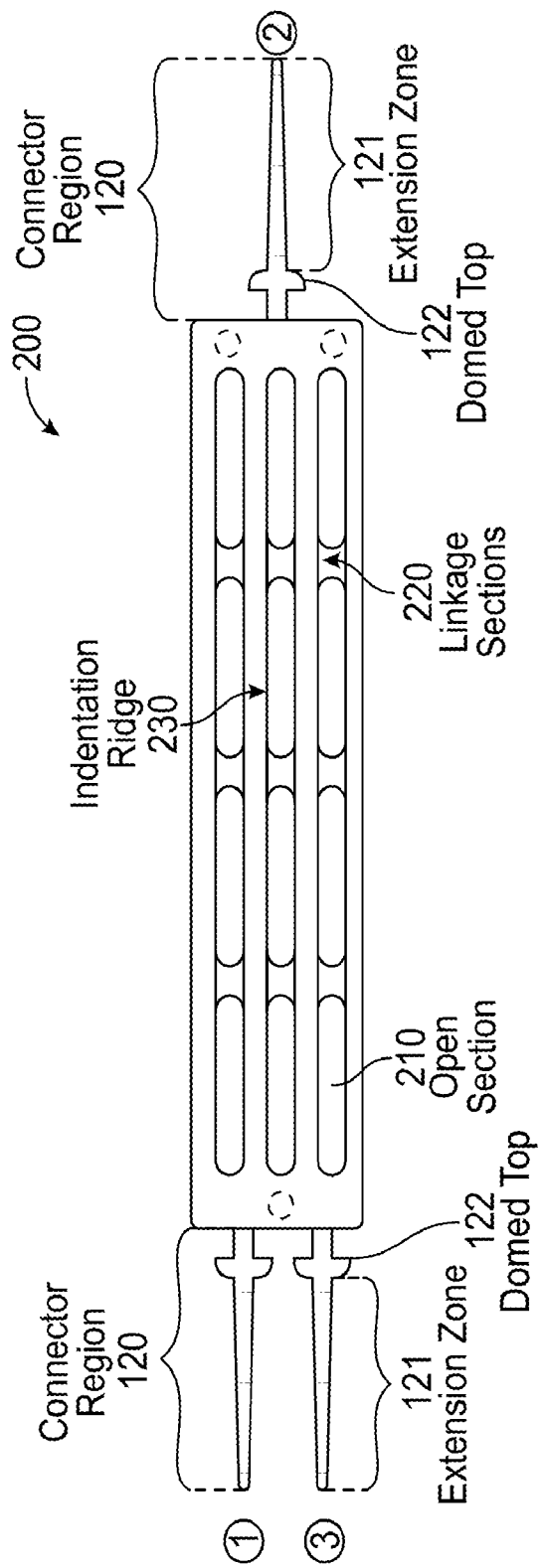

FIG. 6B shows the scleral buckle with a connector region flattened out. The connector region is disposed perpendicularly on or near the first end and the second end. The connector region has an extension zone and a domed top.

Figure 7A:
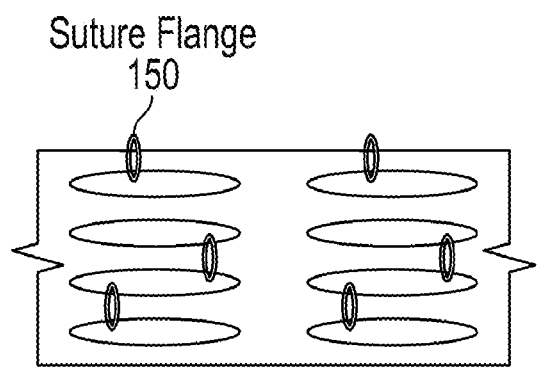
Figure 7B:
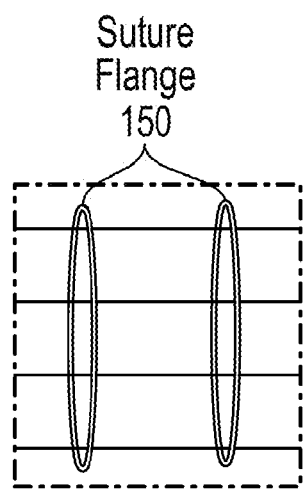

FIGS. 7A-7B show a non-limiting example of how the scleral buckle can be fixed onto the sclera of the eye with suture flange.

Figure 8A:
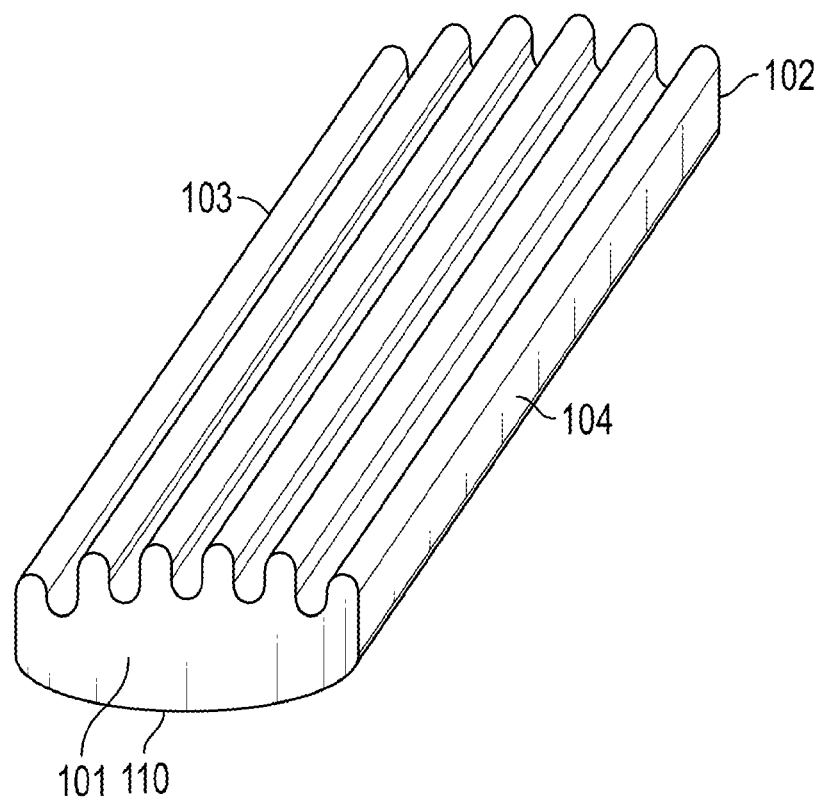
Figure 8B:
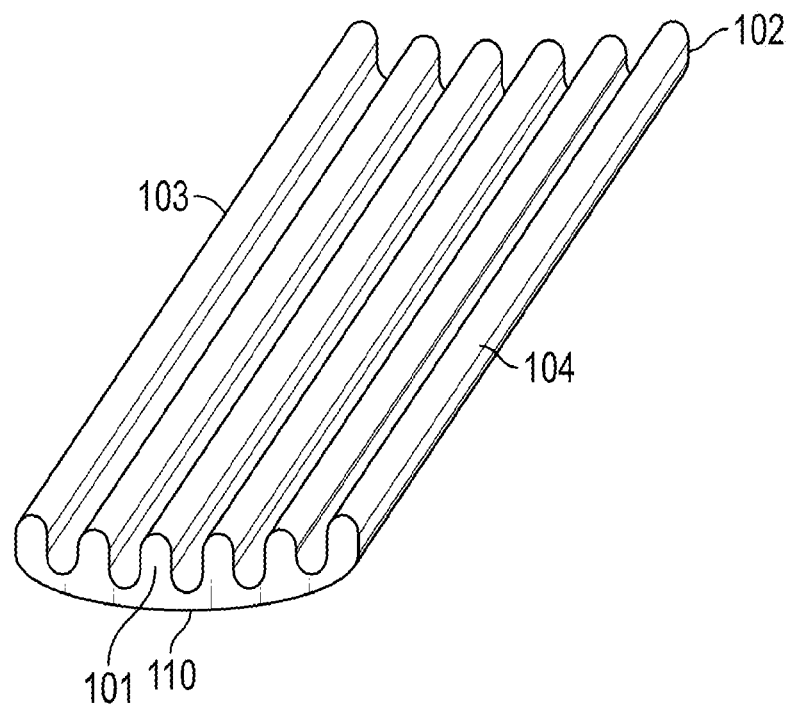

FIGS. 8A-8B show isometric views of embodiments of the scleral buckle having circumferential ridges wherein the interior surface is convex (FIG. 8A) or concave (FIG. 8B). In other, the exterior surface may be flat like in FIG. 4A, instead of curved.

DETAILED DESCRIPTION OF THE INVENTION

Following is a list of elements corresponding to a particular element referred to herein:

100,200 Scleral buckle
101 Scleral buckle first end
102 Scleral buckle second end
103 Scleral buckle third end
104 Scleral buckle fourth end
110 Scleral buckle exterior surface
111 Scleral buckle interior surface
120 Connector Region
121 Extension Zone
122 Domed Top
130 Groove
140 Tapered Region
150 Suture Flange
160 Raised protuberances
161 Circumferential ridges
162 Axial ridges
210 Open Section
220 Linkage Section
230 Indentation Ridges Referring now to FIGS. 1A-8B, the present invention features a scleral buckle design that allows for the lengthening or shortening of the eye to prevent/repair retinal detachment, adjust refractive error and prevent the induction of refractive error by a scleral buckle.

Figure 1A:
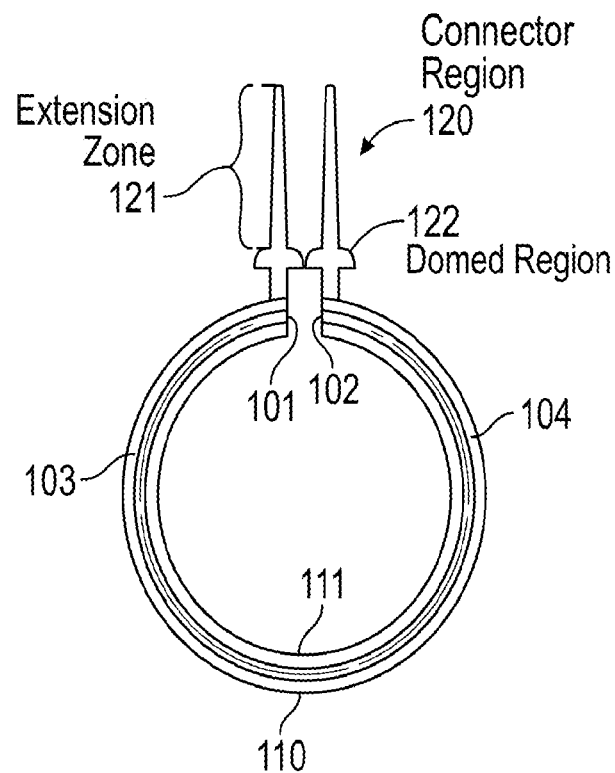
Figure 1B:
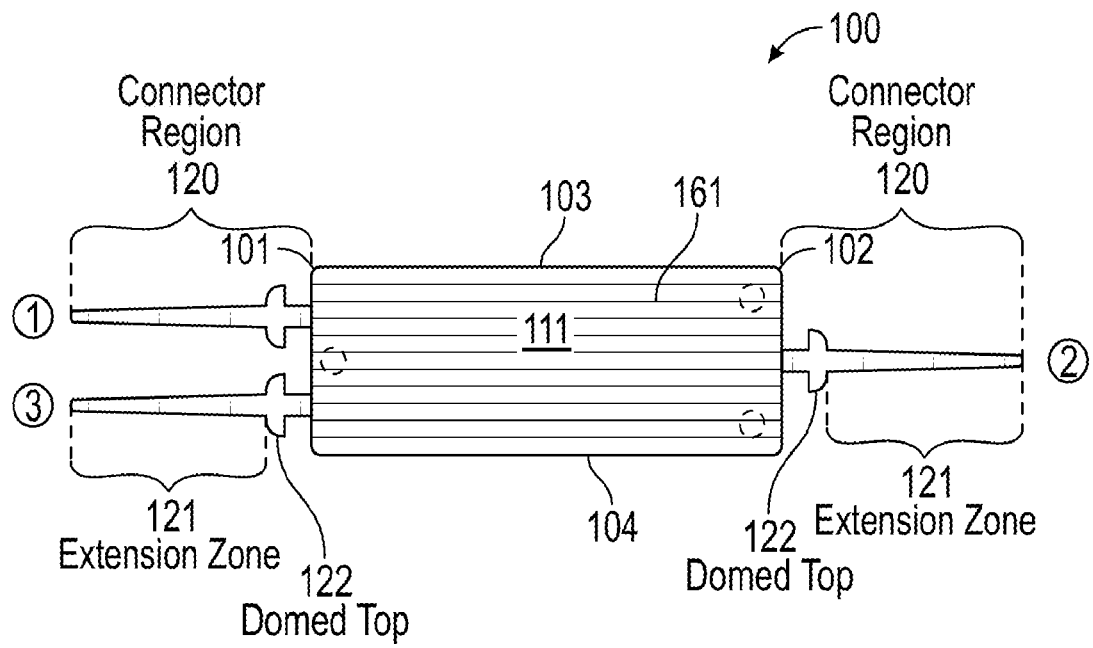

In some embodiments, the present invention may features a scleral buckle (100) comprising a scleral buckle first end (101) and an opposite scleral buckle second end (102), a scleral buckle third end (103) and an opposite scleral buckle fourth end (104), a scleral buckle exterior surface (110) and an opposite scleral buckle interior surface (111) (FIGS. 1A-1B). In some embodiments, the scleral buckle interior surface (111) contains a plurality of protuberances disposed thereon. In further embodiments, the scleral buckle (100) is adapted to be wrapped around the eye by the scleral buckle first end (101) and the scleral buckle second end (101) being brought and held together such that the plurality of protuberances on the interior surface (111) makes contact with a surface of the eye.

In some embodiments, the scleral buckle (100, 200) comprises a connector region (120) disposed perpendicularly at or near the scleral buckle first end (101) and at or near the scleral buckle second end (102). In some embodiments, the connector region (120) comprises a domed top (122) attached to an extension zone (121) (FIG. 1B). In other embodiments the scleral buckle first end (101) and scleral buckle second end (102) are shorter than the scleral buckle third end (103) and scleral buckle fourth end (104). In further embodiments, the scleral buckle (100) is adapted to be wrapped around the eye by the scleral buckle first end (101) and the scleral buckle second end (102) being brought and held together.

In other embodiments, the scleral buckle (100) comprises a groove (130) disposed along the scleral buckle exterior surface (110) (FIGS. 2A-2B). In another embodiment, a silicone band is placed inside the groove (130). In further embodiments, scleral buckle (100) is adapted to be wrapped around the eye by the scleral buckle first end (101) and the scleral buckle second end (102) being brought and held together by a silicon strip inside the groove (130) which is fastened with a silicone tube as one skilled in the art would do.

In other embodiments, the present invention may feature a scleral buckle (200) (FIGS. 5A and 6A) comprising a scleral buckle first end (101) and an opposite scleral buckle second end (102), a scleral buckle third end (103) and an opposite scleral buckle fourth end (104), a scleral buckle exterior surface (110) and an opposite scleral buckle interior surface (111). The scleral buckle (200) may comprise plurality of linkage sections (220) running perpendicular between the scleral buckle third end (103) and the scleral buckle forth end (104). In some embodiments, the scleral buckle (200) comprises a series of indentation ridges (230) running parallel between the scleral buckle third end (103) and the scleral buckle forth end (104) wherein each indentation ridge (230) is in between the linkage sections (220). In some embodiments, the scleral buckle comprises a plurality of open sections (210) between the indentation ridges (230) and the linkage sections (220) (FIG. 5B). In further embodiments, the scleral buckle (200) is adapted to be wrapped around the eye by the scleral buckle first end and the scleral buckle second end being brought and held together.

In some embodiments, the scleral buckle (200) comprises a connector region (120) disposed perpendicularly on the scleral buckle at or near the scleral buckle first end (101) and at or near the scleral buckle second end (102), a connector region (120) comprising a domed top (122) attached to an extension zone (121) (FIG. 6B). In other embodiments the scleral buckle first end (101) and scleral buckle second end (102) are shorter than the scleral buckle third end (103) and scleral buckle fourth end (104). In further embodiments, the scleral buckle (100) is adapted to be wrapped around the eye by the scleral buckle first end (101) and the scleral buckle second end (102) being brought and held together.

Without wishing to limit the invention, the scleral buckle (200) allows for a lower profile and easier installation onto the eye. In some embodiments, the scleral buckle (200) may have a series of indentation ridges attached at regular intervals to allow for a thinner, more open design (FIGS. 5B and 6B).

In some embodiments, the scleral buckle first end (101) and scleral buckle second end (102) are shorter than the scleral buckle third end (103) and scleral buckle fourth end (104). As used herein "aspect ratio" may refer to the ratio of the scleral buckle's (100, 200) longer side to its shorter side (the ratio of length to width of the scleral buckle). In some embodiments, the aspect ratio of the scleral buckle (100, 200) is at least 2:1. In some embodiments, the aspect ratio of the scleral buckle (100, 200) is at least 3:1. In some embodiments, the aspect ratio of the scleral buckle (100, 200) is at least 4:1. In some embodiments, the aspect ratio of the scleral buckle (100, 200) is at least 5:1. In some embodiments, the aspect ratio of the scleral buckle (100, 200) is about 2:1. In some embodiments, the aspect ratio of the scleral buckle (100, 200) is about 3:1. In some embodiments, the aspect ratio of the scleral buckle (100, 200) is about 4:1.

In some embodiments, the present invention scleral buckle designs (100, 200) take into consideration a number of variables, including but not limited to equatorial ocular diameter, chord length of band cross section, width of ridges on ocular surface, height of ridges, spacing of ridges, outer surface anterior-posterior contour, and inner anterior-posterior contour. In some embodiments, these variables help the scleral buckle (100, 200) to accommodate for the natural variations in eye circumference that exist between individuals.

As used herein "equatorial ocular diameter" or "ocular diameter" may refer to horizontal diameter (from side to side, or top to bottom, or oblique position) of the eye. In some embodiments, the equatorial ocular diameter of an eye may range from 20 mm to 34 mm. As used herein "chord length of band cross section" may refer to the linear length between two anterior-posterior points on a scleral buckle. In some embodiments, the chord length of band cross section may range from 1 mm to 2 cm. As used herein "outer surface anterior-posterior contour" may refer to the anterior-posterior contour of the outer (non-ocular) surface of a scleral buckle. In some embodiments, the outer surface anterior-posterior contour may be convex or flat which may prevent friction on Tenon's capsule or conjunctiva. As used herein "inner anterior-posterior contour (in contact with ocular surface)" may refer to anterior-posterior contour of the inner surface of a scleral buckle. In some embodiments, the inner anterior-posterior contour may be concave, convex, or flat. As used herein "axial length" may refer to the linear distance from the front of the cornea to either the retinal surface of the eye or the posterior surface of the sclera.

In some embodiments, emmetropia occurs where the focusing power of the eye is correct for the length of the eye. In some embodiments, emmetropic eyes have normal axial lengths. In other embodiments emmetropic eyes may have an axial length of about 23.5 mm. In some embodiment emmetropic eyes may have normal axial lengths and an increase in ocular equatorial diameter. In some embodiments, the scleral buckle (100, 200) is effective for reducing the equatorial ocular diameter without increasing the axial length. In other embodiments, the scleral buckle (100, 200) is effective for reducing the equatorial ocular diameter without inducing the axial length elongation.

In some embodiments, myopia or near sightedness is a disease in which images are focused on a point inside the eye rather than being focused on the retina. In some embodiments, myopia or near sightedness, occurs when the focusing power of the eye is too strong for the length of the eye. In some embodiments, myopes focus an image in front of the retina and require a concave lens (negative diopter lens) to increase the focal length and focus light on the retina. In some embodiments, the scleral buckle (100, 200), is effective for alleviating myopia. In some embodiments, myopia is caused by an increase in equatorial diameter and axial length. In some embodiments, myopia is caused by a global expansion of the eye, with an increase in the length, width, and height of the eye. In other embodiments, myopia is cause by an increase in axial length. In some embodiments, the myopic eyes have an axial length greater than 23.5 mm. In some embodiments, myopia is caused by axial elongation with no increase in height or width of the eye. In some embodiments, the scleral buckle (100, 200), is effective in reducing the ocular diameter and reducing the axial length. In some embodiments, the scleral buckle (100, 200), is effective for primarily reducing the axial length as well as to reduce the ocular diameter.

Without wishing to be bound to a particular theory or mechanism, it is believed that the present invention is the first scleral buckle that is capable of shortening the axial length of an eye, thereby alleviating myopia. The present invention therefore offers an alternative to more traditional forms of surgical treatments for myopia, such as laser-assisted in situ keratomileusis (LASIK) or photo refractive keratectomy (PRK), particularly in patients with severe myopia (greater than 6 diopters), who are at increased risk for RRD due to the shape and thickness of their eyes. In those patient subpopulations, this invention not only provides a method of alleviating myopia but also of preventing or alleviating RRD.

In some embodiments, hyperopia, or farsightedness, is a disease in which light is focused on a point behind the eye rather than on the retina. In some embodiments, hyperopia, or farsightedness occurs when the focusing power of the eye is too weak for the length of the eye. In some embodiments, hyperopes focus an image behind the retina and require a convex lens (positive diopter lens) to decrease the focal length and focus light on the retina. In some embodiments, the scleral buckle (100, 200) is effective at alleviating hyperopia. In further embodiments, hyperopia is causes by a decrease in axial length. In some embodiments, the have an axial length less than 23.5 mm. In some embodiments, hyperopic eyes may have enlarged equatorial ocular diameters. In other embodiments, hyperopic eye may require reduction of equatorial ocular diameter for the treatment or prevention of retinal detachment. In some embodiments, the scleral buckle (100, 200), is effective for reducing equatorial ocular diameter or the treatment or prevention of retinal detachment.

In some embodiments, the choice of scleral buckle (100, 200) design depends on the combination of axial length of equatorial diameter of the eye. This allows for the present scleral buckle designs to be utilized with a wide variety of eye shapes and sizes.

In some embodiments, the scleral buckle (100, 200) effective for alleviating and preventing retinal detachment. In some embodiments, the scleral buckle (100, 200) is effective for the adjustment of refractive error. In further embodiments, the scleral buckle (100, 200) effective for preventing the refractive error that may be caused by a scleral buckle.

In some embodiments, the connector region (120) is self-locking and can be used to attach the scleral buckle first end (101) to the scleral buckle second end (102) to achieve a fix ocular diameter (FIGS. 3A-3B). In some embodiments, the scleral buckle first end (101) has two connector regions (120) perpendicularly attached at or near the first end (101) and the scleral buckle second end (102) has one connector region (120) perpendicularly attached at or near the second end (102) (FIGS. 1B & 3A). In other embodiments, the scleral buckle second end (102) has two connector regions (120) perpendicularly attached at or near the second end (102) and the scleral buckle first end (101) has one connector region (120) perpendicularly attached at or near the first end (101). In some embodiments, the connector region comprises a domed top (122) attached to an extension zone (121) (FIG. 3B). In some embodiments, the extension zone (121) disposed on the scleral buckle second end (102) passes through a hole at or near the center of the scleral buckle first end (101). In some embodiments, the extension zone (121) may be smaller than the hole disposed at or near the center of the scleral buckle first end (101) and become larger/wider the close it gets to the domed top (122) of the connector region (120). In some embodiments, the domed top (122) has a curved upper surface that may be pulled through the hole on the scleral buckle first end (101). In some embodiment excess material from the extension zone (121) may be cut off after domed top is pulled through the hole on the scleral buckle first end (101). In some embodiments, the domed top (122) provides a smooth surface for the conjunctiva and Tenon's capsule to move over. The extension zone (121) disposed on or near the scleral buckle first end (100) is passed through a hole at or near the edge of the scleral buckle second end (102) (at or near the corner made from the scleral buckle second end (102) and the scleral buckle third end (103) and/or at or near the corner made from the scleral buckle second end (102) and the scleral buckle fourth end (104)).

In some embodiments, the scleral buckle interior surface (111) comprises a plurality of protuberances. In some embodiments, the scleral buckle interior surface (111) comprises a plurality of raised protuberances (160) extending from the scleral buckle first end (101) to the scleral buckle second end (102) and from the scleral buckle third end (103) to the scleral buckle fourth end (104). In some embodiment the plurality of raised protuberances (160) are uniform (FIG. 4C). In some embodiment the plurality of raised protuberances (160) are irregular (FIG. 4D). Without wishing to limit the present invention to any theory or mechanism, the raised protuberances (160) of the present invention are effective to both prevent or alleviate retinal detachment, including rhegmatogenous retinal detachment, and to alleviate myopia. In some embodiments, the plurality of raised protuberances of said scleral buckle is effective for alleviating myopia by reducing the axial length of the eye, thereby allowing the eye's lens to focus light more posteriorly in the eye, thereby focusing said light on the eye's retina. Without wishing to limit the present invention to any theory or mechanism, the plurality of raised protuberances is believed to allow for controlled reduction of circumference and axial length simultaneously.

In some embodiments, the raised protuberances (160) are separated by a spacing of 500 µm. In some embodiments, the raised protuberances (160) are separated by a spacing of 10 mm. In some embodiments, the raised protuberances (160) are separated by a spacing of 100 mm. In some embodiments, the raised protuberances (160) are separated by a spacing of 500 mm. In some embodiments, the raised protuberances (160) are separated by a spacing of 1 cm. In some embodiments, the spacing separating the raised protuberances (160) is between 500 µm to 1 cm. In some embodiments, the raised protuberances (160) may be spaced apart from one another in a uniform manner. For example, the raised protuberances (160) may be spaced linearly along the scleral buckle third end (103) and/or the scleral buckle fourth end (104). For example, the plurality of raised protuberances may all be spaced linearly along the scleral buckle third end (103) and/or scleral buckle fourth end (104) 5 mm apart from one another. In some embodiments, the raised protuberances (160) may be spaced apart from one another in a varying or irregular manner. For example, the linear spacing along the scleral buckle third end (103) and/or scleral buckle fourth end (104) of a first raised protuberance (160) and a second raised protuberance (160) may be 0.5 mm, while the spacing between a third raised protuberance (160) and a fourth raised protuberance (160) may be 2 mm.

In some embodiments, the raised protuberances (160) are 500 µm in width. In some embodiments, the raised protuberances (160) are 10 mm in width. In some embodiments, the raised protuberances (160) are 100 mm in width. In some embodiments, the raised protuberances (160) are 500 mm in width. In some embodiments, the raised protuberances (160) are 1 cm in width. In some embodiments, the raised protuberances (160) are 2 cm in width. In some embodiments, the width of the raised protuberances (160) is about 500 µm to about 2 cm in width.

In some embodiments, the plurality of raised protuberances (160) is 500 µm in height. In some embodiments, the raised protuberances (160) are 10 mm in height. In some embodiments, the raised protuberances (160) are 100 mm in height. In some embodiments, the raised protuberances (160) are 500 mm in height. In some embodiments, the raised protuberances (160) are 1.0 cm in height. In some embodiments, the height of the raised protuberances (160) is between 500 µm to 1.0 cm. In some embodiments, the plurality of raised protuberances (160) may be of uniform height. In some embodiments, the raised protuberances (160) may be of varying or irregular height. For example, a portion of the raised protuberances (160) may be 0.5 mm in height, while another portion of the raised protuberances (160) may be 1.0 mm in height, and so on.

In some embodiments, the plurality of raised protuberances (160) may be of uniform shape (FIG. 4C). For example, the raised protuberances (160) may all have a semicircular or circular cross section. In some embodiments, the raised protuberances (160) may be of varying or irregular shape (FIG. 4D). For example, the raised protuberances (160) may have a complex and irregular shape.

In some embodiments, the scleral buckle design (100, 200) may have 1 raised protuberance (160). In some embodiments, the scleral buckle design (100, 200) may have 10 raised protuberances (160). In some embodiments, the scleral buckle design (100, 200) may have raised protuberances (160). In some embodiments, the scleral buckle design (100, 200) may have raised protuberances (160). In some embodiments, the scleral buckle design (100, 200) may have raised protuberances (160). In some embodiments, the scleral buckle design (100, 200) may have raised protuberances (160). In some embodiments, the scleral buckle design (100, 200) may have raised protuberances (160). In some embodiments, the scleral buckle design (100, 200) may have about 1-200 raised protuberances (160).

In some embodiments, the scleral buckle interior surface (111) comprises a plurality of protuberances. In one embodiment, the plurality of protuberances comprises parallel ridges (161) extending circumferentially from the scleral buckle first end (101) to the scleral buckle second end (102) (FIG. 4A). In some embodiments, the circumferential parallel ridges (161) and the grooves in between create a bellows-like surface on the scleral buckle interior surface (111). In some embodiments, the circumferential ridges (161) appearance can be described as corrugated or accordion-like. Without wishing to limit the present invention to any theory or mechanism, said scleral buckle (100) featuring a plurality of circumferential ridges (161) is effective for alleviating and preventing retinal detachment and is also effective for alleviating myopia by reducing the axial length of the eye, thereby allowing the eye's lens to focus light more posteriorly in the eye, thereby focusing said light on the eye's retina. Without wishing to limit the present invention to any theory or mechanism, the sclera of the eye will be indented by the circumferential ridges (161) of the scleral buckle, thereby affecting the axial length of the eye. Without wishing to limit the present invention to any theory or mechanism, embodiments of the present invention containing circumferential ridges (161) will thereby affect the axial length of the eye.

In some embodiments, the circumferential ridges (161) are separated by a spacing of 500 µm. In some embodiments, the circumferential ridges (161) are separated by a spacing of 10 mm. In some embodiments, the circumferential ridges (161) are separated by a spacing of 100 mm. In some embodiments, the circumferential ridges (161) are separated by a spacing of 500 mm. In some embodiments, the circumferential ridges (161) are separated by a spacing of 1 cm. In some embodiments, the spacing separating the circumferential ridges (161) is about 500 µm to about 1 cm. In some embodiments, the circumferential ridges (161) may be spaced apart from one another in a uniform manner (FIG. 4A). In some embodiments, the circumferential ridges (161) may be spaced linearly along the scleral buckle first end (101) and/or the scleral buckle second end (102). For example, the circumferential ridges (161) may all be spaced linearly along the scleral buckle first end (101) and/or scleral buckle second end (102) and about 5 mm apart from one another. In some embodiments, the circumferential ridges (161) may be spaced apart from one another in a varying or irregular manner. For example, the linear spacing along the scleral buckle first end (101) and/or scleral buckle second end (102) of a first circumferential ridge (161) and a second circumferential ridge (161) may be 0.5 mm, while the spacing between a third circumferential ridge (161) and a fourth circumferential ridge (161) may be 2 mm.

In some embodiments, the circumferential ridges (161) are 500 µm in width. In some embodiments, the circumferential ridges (161) are 10 mm in width. In some embodiments, the circumferential ridges (161) are 100 mm in width. In some embodiments, the circumferential ridges (161) are 500 mm in width. In some embodiments, the circumferential ridges (161) are 1.0 cm in width. In some embodiments, the circumferential ridges (161) are 2.0 cm in width. In some embodiments, the width of the circumferential ridges (161) is about 500 µm to about 2.0 cm in width.

In some embodiments, the circumferential ridges (161) are 500 µm in height. In other embodiments, the circumferential ridges (161) are 10 mm in height. In some embodiments, the circumferential ridges (161) are 100 mm in height. In some embodiments, the circumferential ridges (161) are 500 mm in height. In some embodiments, the circumferential ridges (161) are 1 cm in height. In some embodiments, the height of the circumferential ridges (161) is about 500 µm to about 1 cm. In some embodiments, the circumferential ridges (161) may be uniform in height. Alternatively, the circumferential ridges (161) may vary in height. For example, a portion of the circumferential ridges (161) may be 500 µm in height, while another portion of the circumferential ridges (161) may be 1 mm in height, and so on.

In some embodiments, the circumferential ridges (161) may be of uniform shape. For example, the circumferential ridges (161) may all have a semicircular cross section. In some embodiments, the circumferential ridges (161) may be of varying or irregular shape. For example, the circumferential ridges (161) may have a complex and irregular shape.

In some embodiments, the scleral buckle design (100, 200) may have 1 circumferential ridge (161). In other embodiments, the scleral buckle design (100, 200) may have 10 circumferential ridges (161). In some embodiments, the scleral buckle design (100, 200) may have 50 circumferential ridges (161) or 100 circumferential ridges (161). In some other embodiments, the scleral buckle design (100, 200) may have 150 circumferential ridges (161) or 200 circumferential ridges (161). In some embodiments, the scleral buckle design (100, 200) may have about 1-200 circumferential ridges (161).

In other embodiments, as shown in FIG. 4B, the scleral buckle interior surface (111) comprises a plurality of axial ridges (162) extending axially from the scleral buckle third end (103) to the scleral buckle fourth end (104). In some embodiments, the axial ridges (163) create a bellows-like surface on the scleral buckle interior surface (111). Without wishing to limit the present invention to any theory or mechanism, said scleral buckle (100) featuring a plurality of axial ridges (162) is effective for alleviating and preventing retinal detachment. Without wishing to limit the present invention to any theory or mechanism, the sclera of the eye will be indented by the axial ridges (162) of the scleral buckle. Without wishing to limit the present invention to any theory or mechanism, embodiments of the present invention containing axial ridges (162) can prevent retinal detachment in a more controlled fashion than prior scleral buckles and circling bands.

In some embodiments, the axial ridges (162) are separated by a spacing of 500 μm. In some embodiments, the axial ridges (162) are separated by a spacing of 10 mm. In some embodiments, the axial ridges (162) are separated by a spacing of 100 mm. In some embodiments, the axial ridges (162) are separated by a spacing of 500 mm. In some embodiments, the axial ridges (162) are separated by a spacing of 1 cm. In some embodiments, the spacing separating the axial ridges (162) is about 500 μm to 1 cm. In some embodiments, the axial ridges (162) may be spaced apart from one another in a uniform manner (FIG. 4B). For example, the axial ridges (162) may be spaced linearly along the scleral buckle third end (103) and/or the scleral buckle fourth end (104). For example, the axial ridges (162) may all be spaced linearly along the scleral buckle third end and (103)/or scleral buckle fourth end (104) 500 μm apart from one another. In some embodiments, the axial ridges (162) may be spaced apart from one another in a varying or irregular manner. For example, the linear spacing along the scleral buckle third end (103) and/or scleral buckle fourth end (104) a first axial ridge (162) and a second axial ridge (162) may be separated by 500 μm, while the spacing between a third axial ridge (162) and a fourth axial ridge (162) may be separated by 2 mm.

In some embodiments, the axial ridges (162) are 500 μm in width. In some embodiments, the axial ridges (162) are 10 mm in width. In some embodiments, the axial ridges (162) are 100 mm in width. In some embodiments, the axial ridges (162) are 500 mm in width. In some embodiments, the axial ridges (162) are 1.0 cm in width. In some embodiments, the axial ridges (162) are 2.0 cm in width. In some embodiments, the width of the axial ridges (162) is about 500 μm and 2.0 cm in width.

In some embodiments, the axial ridges (162) are 500 μm in height. In some embodiments, the axial ridges (162) are 10 mm in height. In some embodiments, axial ridges (162) are 100 mm in height. In some embodiments, the axial ridges (162) are 500 mm in height. In some embodiments, the axial ridges (162) are 1 cm in height. In some embodiments, the height of the axial ridges (162) is between 500 μm to 1 cm. In some embodiments, the axial ridges (162) may be uniform in height. In some embodiments, the axial ridges (162) may be irregular in height. For example, a portion of the axial ridges (162) may be 500 μm in height, while another portion of axial ridges (162) may be 1 mm in height, and so on.

In some embodiments, the axial ridges (162) may be of uniform shape. For example, the axial ridges (162) may all have a semicircular cross section. In some embodiments, the axial ridges (162) may be of varying or irregular shape. For example, the axial ridges (162) may have a complex and irregular shape.

In some embodiments, the scleral buckle design (100, 200) may have 1 axial ridge (162). In some embodiments, the scleral buckle design (100, 200) may have 10 axial ridges (162). In some embodiments, the scleral buckle design (100, 200) may have 50 axial ridges (162). In some embodiments, the scleral buckle design (100, 200) may have 100 axial ridges (162). In some embodiments, the scleral buckle design (100, 200) may have 150 axial ridges (162). In some embodiments, the scleral buckle design (100, 200) may have 200 axial ridges (162). In some embodiments, the scleral buckle design (100, 200) may have about 1-200 axial ridges (162).

In some embodiments, the scleral buckle (200) comprises a series of indentation ridges (230). In some embodiments, the indentation ridges (230) are separated by a spacing of 500 μm. In some embodiments, the indentation ridges (230) are separated by a spacing of 10 mm. In some embodiments, the indentation ridges (230) are separated by a spacing of 100 mm. In some embodiments, the indentation ridges (230) are separated by a spacing of 500 mm. In some embodiments, the indentation ridges (230) are separated by a spacing of 1 cm. In some embodiments, the spacing separating the indentation ridges (230) is about 500 μm to about 1 cm. In some embodiments, the indentation ridges (230) may be spaced apart from one another in a uniform manner (FIG. 5B and FIG. 6B). In some embodiments, the indentation ridges (230) may be spaced linearly along the scleral buckle first end (101) and/or the scleral buckle second end (102). For example, the indentation ridges (230) may all be spaced linearly along the scleral buckle first end (101) and/or scleral buckle second end (102) and about 5 mm apart from one another. In some embodiments, the indentation ridges (230) may be spaced apart from one another in a varying or irregular manner. For example, the linear spacing along the scleral buckle first end (101) and/or scleral buckle second end (102) of a first indentation ridge (230) and a second indentation ridge (230) may be 0.5 mm, while the spacing between a third indentation ridge (230) and a fourth indentation ridge (230) may be 2 mm.

In some embodiments, the indentation ridges (230) are 500 μm in width. In some embodiments, the indentation ridges (230) are 10 mm in width. In some embodiments, the indentation ridges (230) are 100 mm in width. In some embodiments, the indentation ridges (230) are 500 mm in width. In some embodiments, the indentation ridges (230) are 1.0 cm in width. In some embodiments, the indentation ridges (230) are 2.0 cm in width. In some embodiments, the width of the indentation ridges (230) is about 500 μm to about 2.0 cm in width.

In some embodiments, the indentation ridges (230) are 500 μm in height. In other embodiments, the indentation ridges (230) are 10 mm in height. In some embodiments, the indentation ridges (230) are 100 mm in height. In some embodiments, the indentation ridges (230) are 500 mm in height. In some embodiments, the indentation ridges (230) are 1 cm in height. In some embodiments, the height of the indentation ridges (230) is about 500 μm to about 1 cm. In some embodiments, the indentation ridges (230) may be uniform in height. Alternatively, the indentation ridges (230) may vary in height. For example, a portion of the indentation ridges (230) may be 500 μm in height, while another portion of the indentation ridges (230) may be 1 mm in height, and so on.

In some embodiments, the indentation ridges (230) may be of uniform shape. For example, the indentation ridges (230) may all have a circular cross section (FIG. 5D). In some embodiments, the indentation ridges (230) may be of varying or irregular shape (FIG. 5C). For example, the indentation ridges (230) may have a complex and irregular shape.

In some embodiments, the scleral buckle design (100, 200) may have 1 indentation ridge (230). In other embodiments, the scleral buckle design (100, 200) may have 10 indentation ridges (230). In some embodiments, the scleral buckle design (100, 200) may have 50 indentation ridges (230) or 100 indentation ridges (230). In some other embodiments, the scleral buckle design (100, 200) may have 150 indentation ridges (230) or 200 indentation ridges (230). In some embodiments, the scleral buckle design (100, 200) may have about 1-200 indentation ridges (230).

In some embodiment the scleral buckle (100) comprises a groove (130) that is 0.5 mm wide. In some embodiment the groove (130) is 1.0 mm wide. In some embodiment the groove (130) is 1.5 mm wide. In some embodiment the groove (130) is 2.0 mm wide. In some embodiment the groove (130) is 2.5 mm wide. In some embodiment the groove (130) is 3.0 mm wide. In some embodiment the groove (130) is 3.5 mm wide. In some embodiment the groove (130) is 4.0 mm wide. In some embodiment the groove (130) is 4.5 mm wide. In some embodiment the groove (130) is 5.0 mm wide. In some embodiment the groove (130) is between 0.5 mm and 5.0 mm wide.

Without wishing to limit the present invention to any theory or mechanism, the shape of the eye will conform to the shape of the surface of the scleral buckle interior surface (111). For example, the eye may be indented in by the raised protuberances (160), or the circumferential ridges (161) or the axial ridges (162). The indentation of the eye will allow for changes in the axial length and/or ocular diameters and/or the circumferential length as well as allows for the prevention or retinal detachment. In some embodiment the scleral buckle exterior surface (110) can also be adjusted for the variation in eye shapes. In some embodiment, the scleral buckle exterior surface (110) can be flat, or convex, or concave.

In some embodiments, the scleral buckle (100, 200) may be made from biocompatible material including, by not limited to, silicone rubber, nylon, polypropylene, or other biocompatible polymers or elastomers.

In further embodiments, the present invention may feature a method of scleral buckling the eye. In some embodiments, the method comprises of inserting the scleral buckle (100, 200) underneath the rectus muscles of the eye, connecting the scleral buckle first end (101) and the scleral buckle second end (101) and suturing the scleral buckle to the sclera with sutures.

In some embodiments, the scleral buckle (100, 200) may be attached the sclera of the patient's eye by a suture flange (131). In some embodiments, the scleral buckle can be attached to the sclera with sutures placed around the entire scleral buckle (FIG. 7B) or can be attached with sutures places around the ridges in FIG. 7A. In some embodiments, the suture flange (131) can be attached in a conventional fashion (FIG. 7B) or can be attached at any of the band location as indicated in FIG. 7A. Without wishing to limit the present invention to any theory or mechanism, this provides a point where the scleral buckle (100, 200) may be attached to the sclera of the eye of a patient, preventing the scleral buckle (100, 200) from shifting its position on the sclera of the patient's eye, due, for instance, to regular events such as friction between the sclera and surrounding tissue, or due to unforeseen events like trauma to the eye.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. The reference numbers recited in the below claims are solely for ease of examination of this patent application, and are exemplary, and are not intended in any way to limit the scope of the claims to the particular features having the corresponding reference numbers in the drawings. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

What is claimed is:

1. A scleral buckle (200) comprising:
 a) a scleral buckle first end (101) and an opposite scleral buckle second end (102);
 b) a scleral buckle third end (103) and an opposite scleral buckle fourth end (104);
 c) a scleral buckle exterior surface (110) and an opposite scleral buckle interior surface (111);
 d) a plurality of linkage sections (220) running perpendicular between the scleral buckle third end (103) and the scleral buckle forth end (104);
 e) a series of indentation ridges (230) running parallel between the scleral buckle third end (103) and the scleral buckle forth end (104), wherein each indentation ridge is in between the linkage sections (220);
 f) a plurality of open sections (210) between the indentation ridges (230) and the linkage sections (220);
 wherein the scleral buckle is adapted to be wrapped around the eye by the scleral buckle first end (101) and the scleral buckle second end (102) being brought and held together.

2. The scleral buckle (200) of claim 1 having an aspect ratio of at least 2:1.

3. The scleral buckle (200) of claim 1 having a connector region (120) disposed on the scleral buckle at or near the scleral buckle first end (101) and the scleral buckle second end (102).

4. The scleral buckle (200) of claim 3, wherein the connector region (120) comprises a domed top (122) attached to an extension zone (121).

5. The scleral buckle (200) of claim 1, wherein the scleral buckle (200) is effective for alleviating myopia or for alleviating hyperopia.

6. The scleral buckle (200) of claim 1, wherein the scleral buckle (200) is effective for alleviating and preventing retinal detachment or for adjustment of refractive error.

7. A method of scleral buckling an eye, comprising providing the scleral buckle (200) of claim 1, inserting the scleral buckle (200) underneath rectus muscles of the eye, connecting the scleral buckle first end (101) and scleral buckle second end (102) and suturing the scleral buckle (200) to the sclera with sutures placed around the indentation ridges and/or the entire scleral buckle.

\* \* \* \* \*